(12) United States Patent  (10) Patent No.: US 6,368,271 B1
Sharratt  (45) Date of Patent: Apr. 9, 2002

(54) METHOD FOR HUMERUS RETRACTION

(75) Inventor: Todd W. Sharratt, Cottage Grove, MN (US)

(73) Assignee: Minnesota Scientific, Inc., St. Paul, MN (US)

( * ) Notice: Subject to any disclaimer, the term of this patent is extended or adjusted under 35 U.S.C. 154(b) by 0 days.

(21) Appl. No.: 09/990,420

(22) Filed: Nov. 21, 2001

Related U.S. Application Data

(63) Continuation-in-part of application No. 09/654,400, filed on Sep. 1, 2000, now Pat. No. 6,315,718.

(51) Int. Cl.⁷ ............................................. A61B 1/32
(52) U.S. Cl. ............................ 600/228; 600/235
(58) Field of Search .......................... 600/201, 227, 600/228, 230, 235; 623/19.11, 19.12, 19.13; 606/90; 128/898, 878; 602/32, 33, 34, 35, 39

(56) References Cited

U.S. PATENT DOCUMENTS

| | | | |
|---|---|---|---|
| 4,261,062 A | 4/1981 | Amstutz et al. | |
| 5,437,677 A | 8/1995 | Shearer et al. | 606/96 |
| 5,454,365 A | 10/1995 | Bonutti | 600/204 |
| 5,507,817 A | 4/1996 | Craig et al. | 623/18 |
| 5,685,826 A | 11/1997 | Bonutti | 600/204 |
| 5,702,486 A | 12/1997 | Craig et al. | 623/23 |
| 5,707,390 A | 1/1998 | Bonutti | 606/204 |
| 5,716,325 A | 2/1998 | Bonutti | 600/204 |
| 5,782,924 A | 7/1998 | Johnson | 623/20 |
| 5,888,196 A | 3/1999 | Bonutti | 600/204 |
| 5,954,739 A * | 9/1999 | Bonutti | 600/207 X |
| 5,961,512 A | 10/1999 | Purnell | 606/1 |
| 6,315,718 B1 * | 11/2001 | Sharratt | 600/228 |

FOREIGN PATENT DOCUMENTS

DE    4103070 A1 *  8/1991   ................. 606/90

* cited by examiner

Primary Examiner—Jeffrey A. Smith
(74) Attorney, Agent, or Firm—Kinney & Lange, P.A.

(57) ABSTRACT

A method for performing surgery on a shoulder joint utilizes one positionable support arm attached to a retractor support apparatus. The method includes incising a patient to expose the shoulder joint. After exposing the shoulder joint, the humeral ball is dislocated from the glenoid cavity. A retractor is mounted to one of the support arms at a proximal end. A humerus retractor blade at a distal end of the humerus retractor engages the humerus. The humerus retractor blade is positioned about the humerus and a mechanical system within the humerus retractor is manipulated to laterally displace the humeral ball from the glenoid cavity.

48 Claims, 6 Drawing Sheets

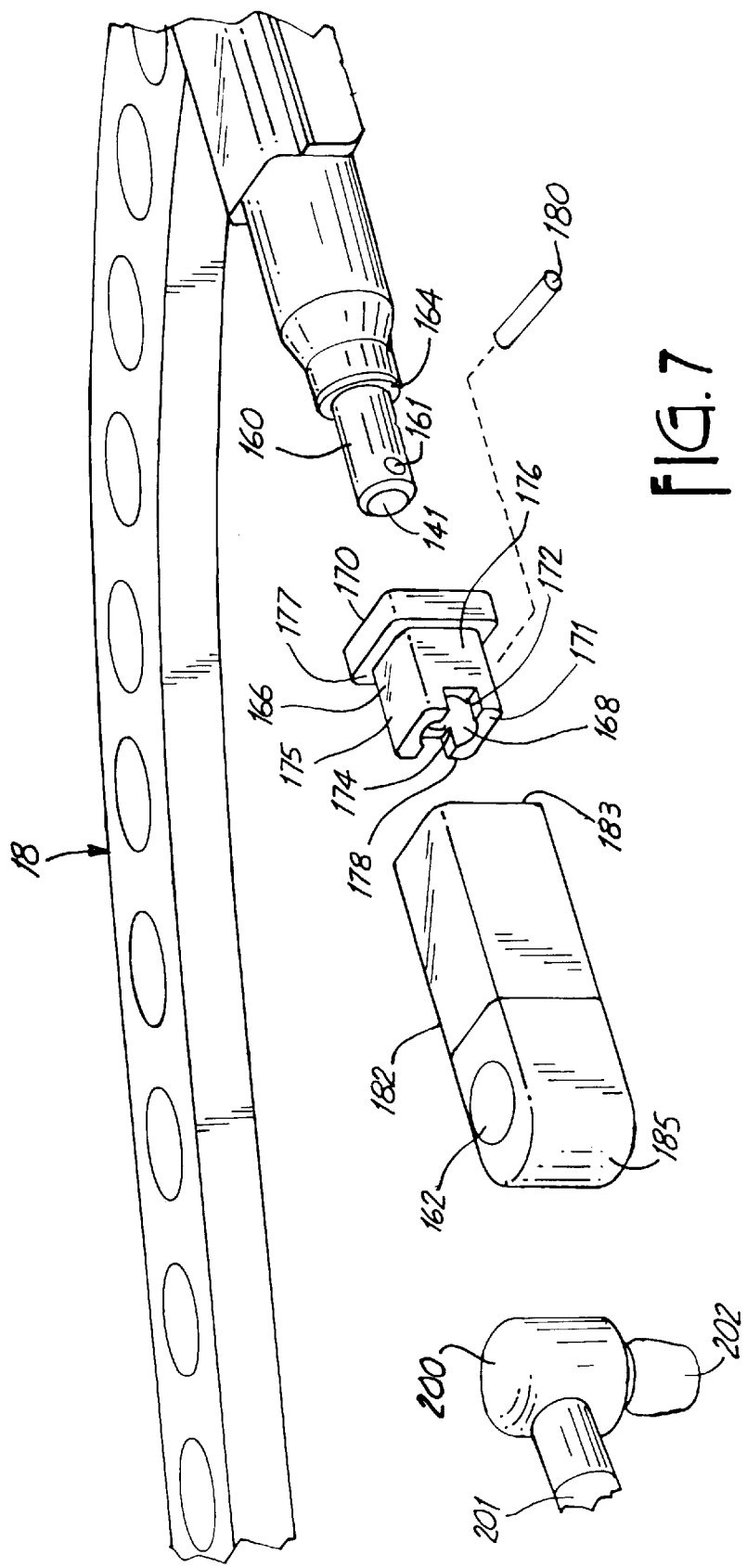

METHOD FOR HUMERUS RETRACTION

CROSS-REFERENCE TO RELATED APPLICATION(S)

The present application is a continuation-in-part of U.S. application Ser. No. 09/654,400 filed on Sep. 1, 2000, now U.S. Pat. No. 6,315,718, and claims priority therefrom.

BACKGROUND OF THE INVENTION

The present invention relates to a method of surgical retraction. In particular, the present invention relates to a method of retracting the humerus during shoulder surgery.

Total shoulder replacement (arthroplasty) operations have been performed for many decades to repair shoulder components. These components include the glenoid cavity (socket portion of the shoulder) and the humeral head (ball portion of the shoulder). The shoulder is typically replaced due to a gradual deterioration or wearing of the glenoid cavity and/or the humeral head or ball. Common causes of the deterioration of the shoulder joint from smooth surfaces where the joint is properly articulating to rough surfaces where articulation of the joint is painful include osteoarthritis, Rheumatoid arthritis as well as trauma which injures the shoulder joint. The deterioration causes either the humeral ball, the glenoid cavity or both the humeral ball and the glenoid cavity become rough which results in pain when the shoulder joint is articulated.

Surgical procedures have been the most successful method to alleviate this type of shoulder pain. Either partial or total shoulder replacement surgery can be performed. In a total shoulder replacement procedure, a cup shaped insert, typically manufactured of polyethylene, is inserted into the worn glenoid cavity and a metal ball is used to replace the humeral head. A partial shoulder replacement is performed when either the humeral ball is replaced or the glenoid cavity is repaired with an insert.

The shoulder replacement surgery is conducted by making an incision through the skin into the front of the shoulder. Typically, the incision is about three inches long. Because of the relatively small size of the incision and the surgical site being on one side of the body, access to the surgical site is limited.

After making the incision through the skin, the surgeon divides the tissue and muscle to expose the shoulder joint. When the humeral ball is replaced, the surgeon separates the humeral bone from the humerus, typically with a bone saw. The surgeon has two options when separating the humeral ball from the humerus. The humeral ball may be separated from the humerus while the humeral ball remains within the glenoid cavity. Alternatively, the humeral ball may be dislocated from the glenoid cavity followed by the humeral ball being separated from the humerus.

After separating the humeral ball from the humerus, the arm is retracted away from the body, or laterally. The arm is usually retracted with a hand-held retractor where the surgeon or an assistant must apply a constant force upon the humerus. One hand-held retractor that is used for retracting the humerus is called a Fakuda blade. A Fakuda blade has a flat surface with a curved end. An aperture is disposed within the Fakuda blade which better grips the humerus than a blade having only a flat surface.

After laterally retracting the humerus, the humeral ball is dislocated from the glenoid cavity, thereby exposing the glenoid cavity for insertion of the cup shaped insert. Additionally, laterally retracting the humerus away from the shoulder joint makes the freshly cut portion of the humerus accessible for replacement of the humeral ball.

The humerus is prepared by hollowing a cavity into the interior of the humerus with a rasp to create a place for the humeral ball component to be attached to the humerus. The metal humeral ball includes a stem which is inserted into the hollowed out cavity in the humerus. The metal humeral ball is fixedly attached to the humerus by techniques which are known in the art including, but not limited to, cement or a non-cement technique, such as bony ingrowth.

Typically, at least two strong people are needed to perform a total shoulder replacement. One person is needed to retract the humerus from the glenoid cavity to gain access to both the glenoid cavity and the humerus. The other person is needed to prepare the glenoid cavity and the humerus for the insert and metal ball, respectively. After the replacement components are inserted, the shoulder is reduced (the humeral component is inserted into the glenoid cavity component) to check the angle and fit of the humeral ball into the glenoid cavity insert. If the shoulder components do not adequately fit, the shoulder is again dislocated, the components readjusted, and the humeral ball is positioned in the glenoid cavity. If the stability and placement of the trial inserts is acceptable, the shoulder is dislocated and the humeral implant stem is placed into and secured within the hollowed cavity of the humerus. The humeral ball is again positioned within the glenoid cavity and the stability of the arthroplasty is confirmed.

Due to the multiple dislocations and insertions of the humeral ball into the glenoid cavity, as well as retracting the humerus, the surgical procedure can become quite physically taxing on the surgeon or surgeons performing it. The surgical procedure requires lifting and moving the patient's arm into multiple positions. At times, the surgeon may need to hold the arm in a selected position for an extended period of time. Depending on the size of the patient, the strenuous activity can lead to fatigue and contribute to surgical error. Additionally, the repeated movement of the arm can cause nerve damage if it is not done precisely and with minimal adjustment. When the surgeon moves the humerus by hand it is common to have continual adjusting occur. Often, the surgeon holding the arm, relaxes or becomes fatigued and allows the arm to move, requiring that the arm be readjusted. The movement can cause the arm to pinch or rub nerves or muscle tissue, possibly causing damage.

BRIEF SUMMARY OF THE INVENTION

The present invention includes a method for performing surgery on a shoulder joint using at least one positionable support arm attached to a retractor support apparatus, where the shoulder joint includes a glenoid cavity, a humerus and a humeral ball attached to the humerus and positioned within the glenoid cavity. The method includes incising a patient to expose the shoulder joint. After exposing the shoulder joint, the humeral ball is dislocated from the glenoid cavity. A retractor is mounted to one of the support arms at a proximal end. A humerus retractor blade at a distal end of the retractor engages the humerus. The humerus retractor blade is positioned about the humerus and a mechanical system within the humerus retractor is manipulated to laterally displace the humeral ball from the glenoid cavity.

BRIEF DESCRIPTION OF THE DRAWINGS

FIG. 7 is a partial perspective view of a mechanism for attaching a retractor blade to the retractor mechanism.

DETAILED DESCRIPTION

Figure 1:
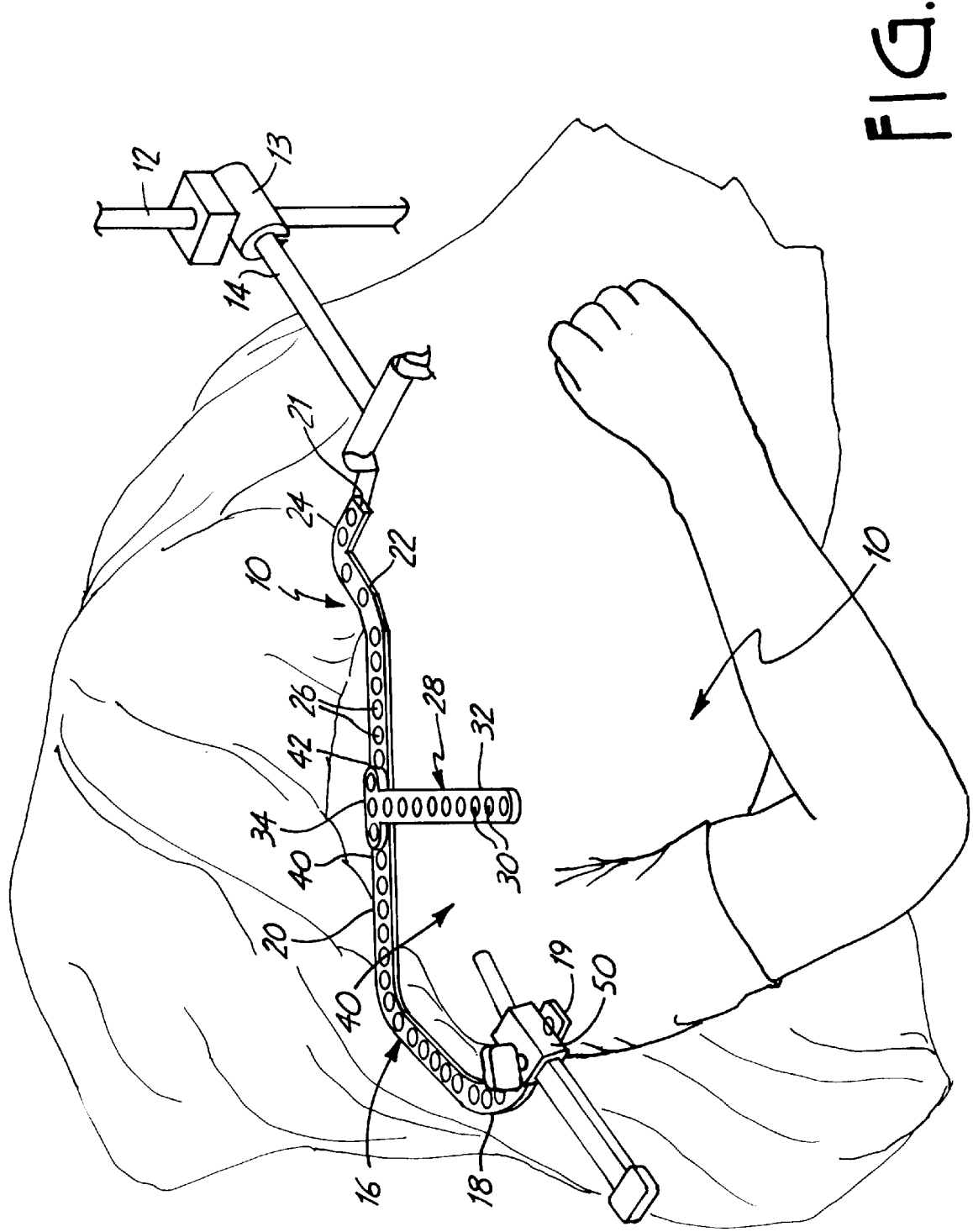
FIG. 1 is a perspective view of a support structure for a shoulder surgery.

The present invention relates to a method for retracting the upper arm or humerus bone during a shoulder surgery as generally illustrated in FIG. 1 at 10. In preparation for a shoulder replacement surgery, a height of a generally J-shaped member 16 is adjusted by clamping the support member 14 in a selected position on a retractor support apparatus 12 with a clamp 13.

To provide adequate support around the shoulder while maintaining access to the shoulder to be operated upon, the generally J-shaped member 16 is attached to the support member 14 as illustrated in FIG. 1. The generally J-shaped member 16 includes an arcuate portion 18 proximate a first end 19, a substantially straight middle portion 20 and an outwardly extending portion 22 proximate a second end 21. An engaging portion 24 which engages the support member 14 is positioned substantially perpendicular to the outwardly extending portion 22. The engaging portion 24 is designed to engage the docking member disclosed in U.S. application Ser. No. 09/654,400 from which this application is a continuation-in-part and which is hereby incorporated by reference in its entirety.

Figure 4:
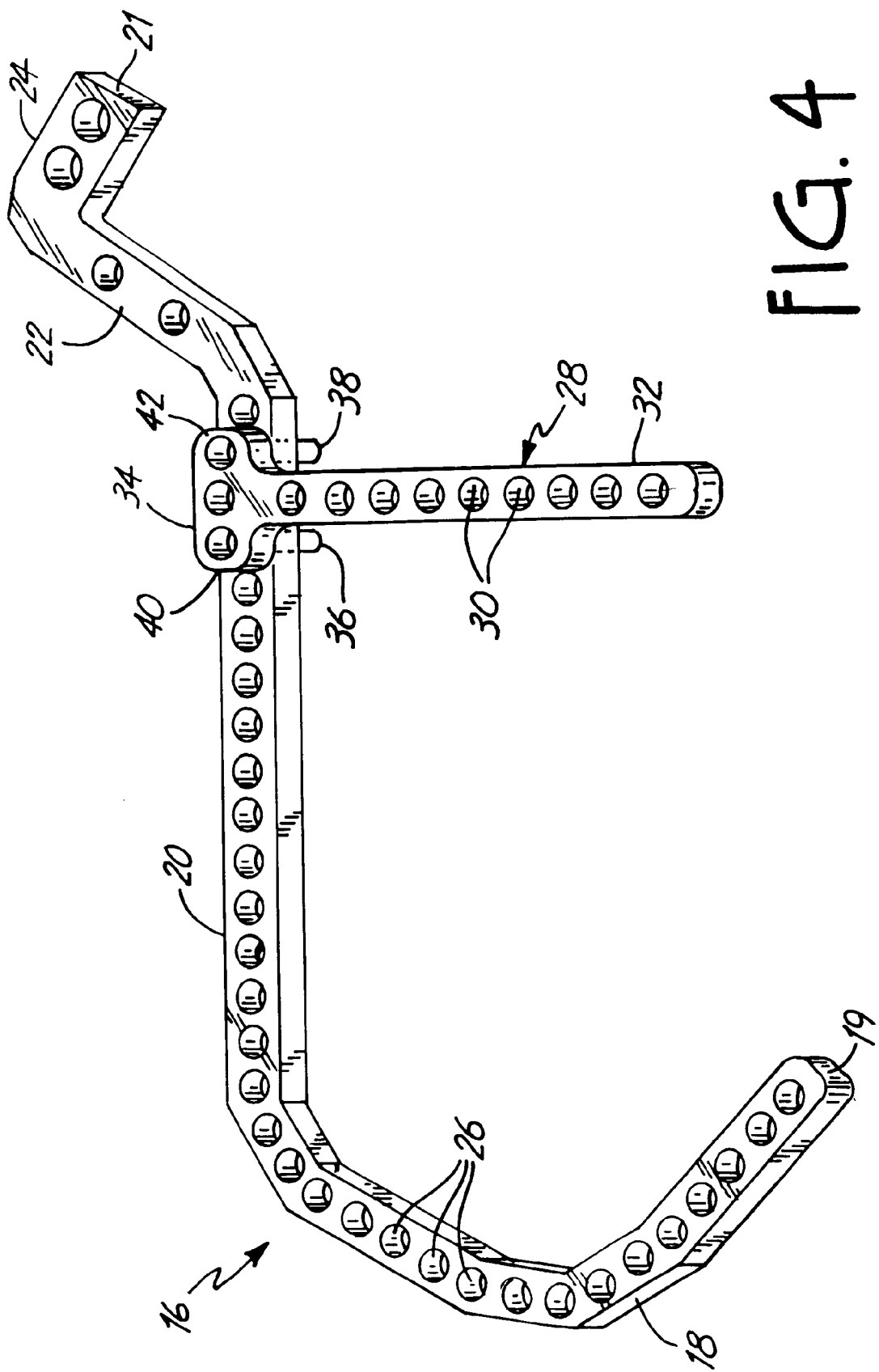
FIG. 4 is a perspective view of the support members for a shoulder operation.

Referring to FIGS. 1 and 4, the generally J-shaped member 16 includes substantially uniformly spaced apart apertures 26 along the arcuate portion 18 proximate a first end 19 and also the substantially straight middle portion 20. A T-shaped member 28 having a plurality of apertures 30 along the long portion 32 of the T-shaped member 28 is operably attached to the generally J-shaped member 16. The T-shaped member 28 includes first and second pegs 36, 38 proximate first and second ends 40, 42, respectively, of a short portion 34, as illustrated in FIG. 4. The first and second pegs 36, 38 engage the uniformly spaced apart apertures 26 in the generally J-shaped member 16 such that the T-shaped member 28 is positionable along the generally J-shaped member 16.

Figure 5:
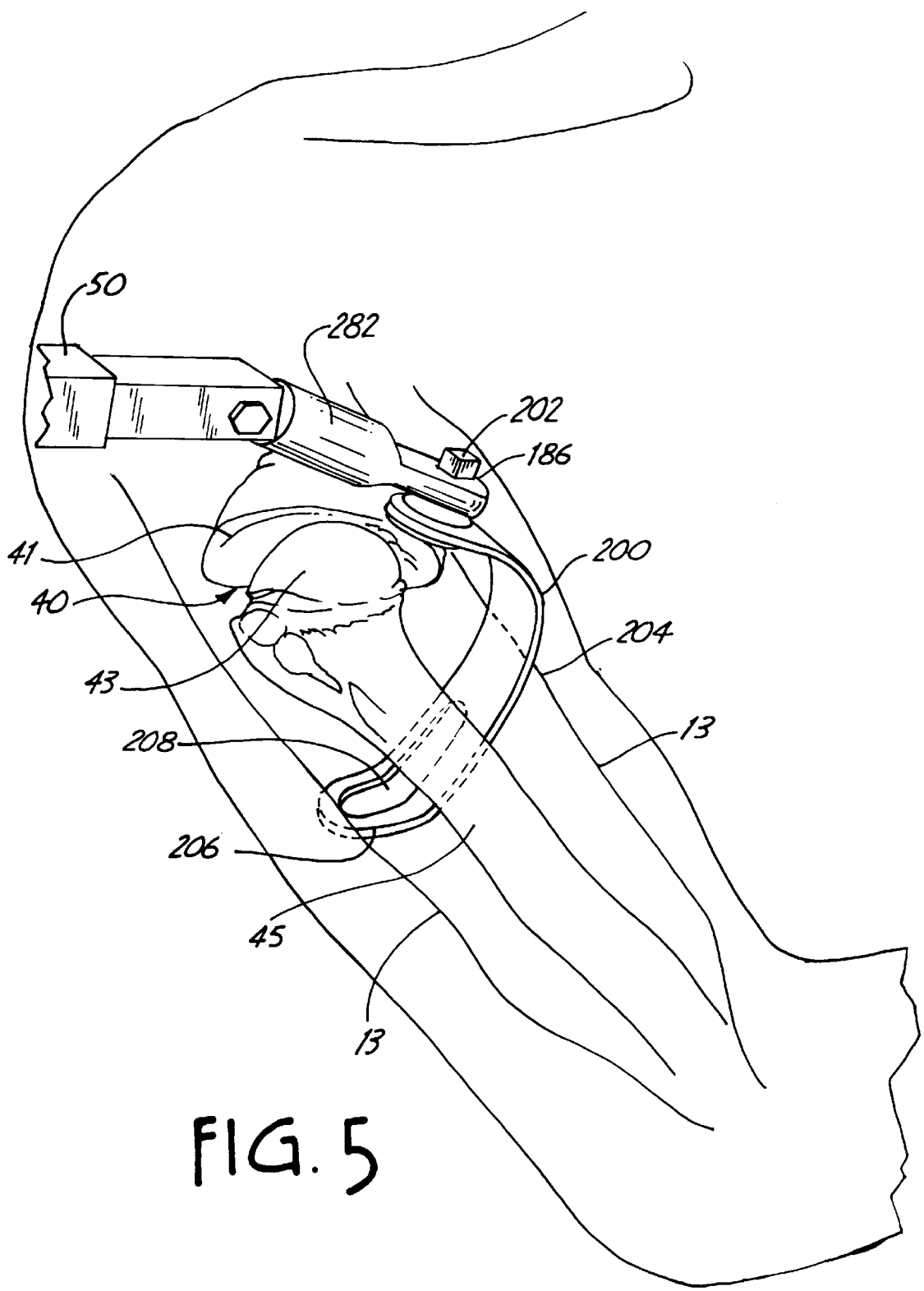
FIG. 5 is a partial perspective view of a humerus being longitudinally retracted from the glenoid cavity with a retractor blade having an aperture therein.

Referring to FIGS. 1 and 5, the surgical procedure begins by adjusting the height of the support structure 14. The generally J-shaped member 16 is rotatably positioned about a shoulder 40 to be surgically repaired. The first and second pegs 36, 38 of the T-shaped member 28 are positioned in a selected position within the plurality of apertures 26 in the generally J-shaped member 16. The combination of the generally J-shaped member 16 and the T-shaped member 28 provide the required support structure for performing the operation while maintaining access to the surgical site. The selected location of the T-shaped member 28 is determined by the type of surgical procedure to be performed, the size of the incision to be made and the size of the patient being operated upon.

Figure 2:
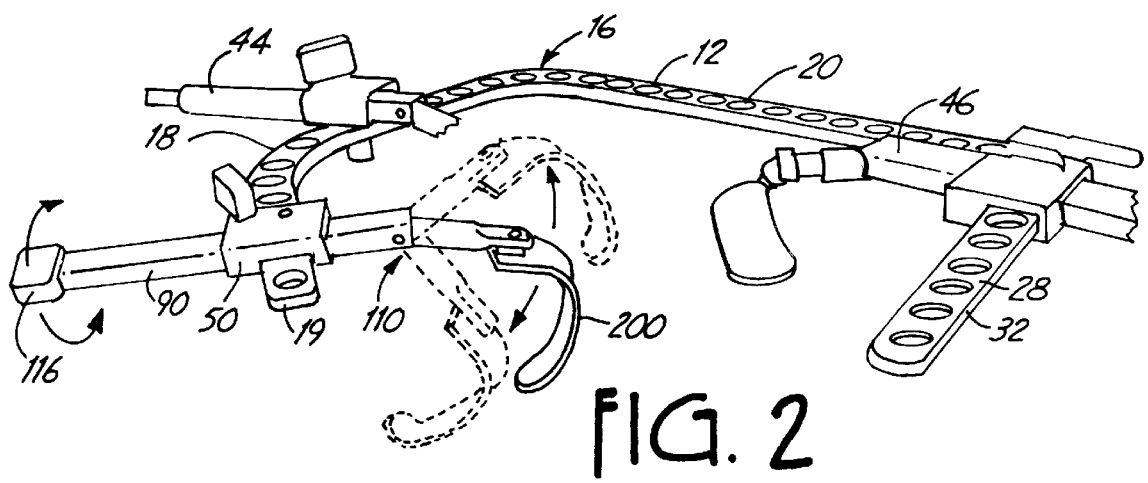
FIG. 2 is a perspective view of a retractor mechanism having an articulated joint for adjusting a height of a retractor blade.

Referring to FIG. 5, an incision 13 is made into the flesh of the patient. Retractors 44, 46, as best illustrated in FIG. 2, are secured to both the generally J-shaped member 16 and the T-shaped member 28 and retract the flesh from the incision 13 thereby exposing the shoulder joint 40. With the shoulder joint 40 exposed, the glenoid cavity 41, the humeral ball 43 and an upper portion of the humerus 45 are viewable through the retracted incision 13.

Figure 6:
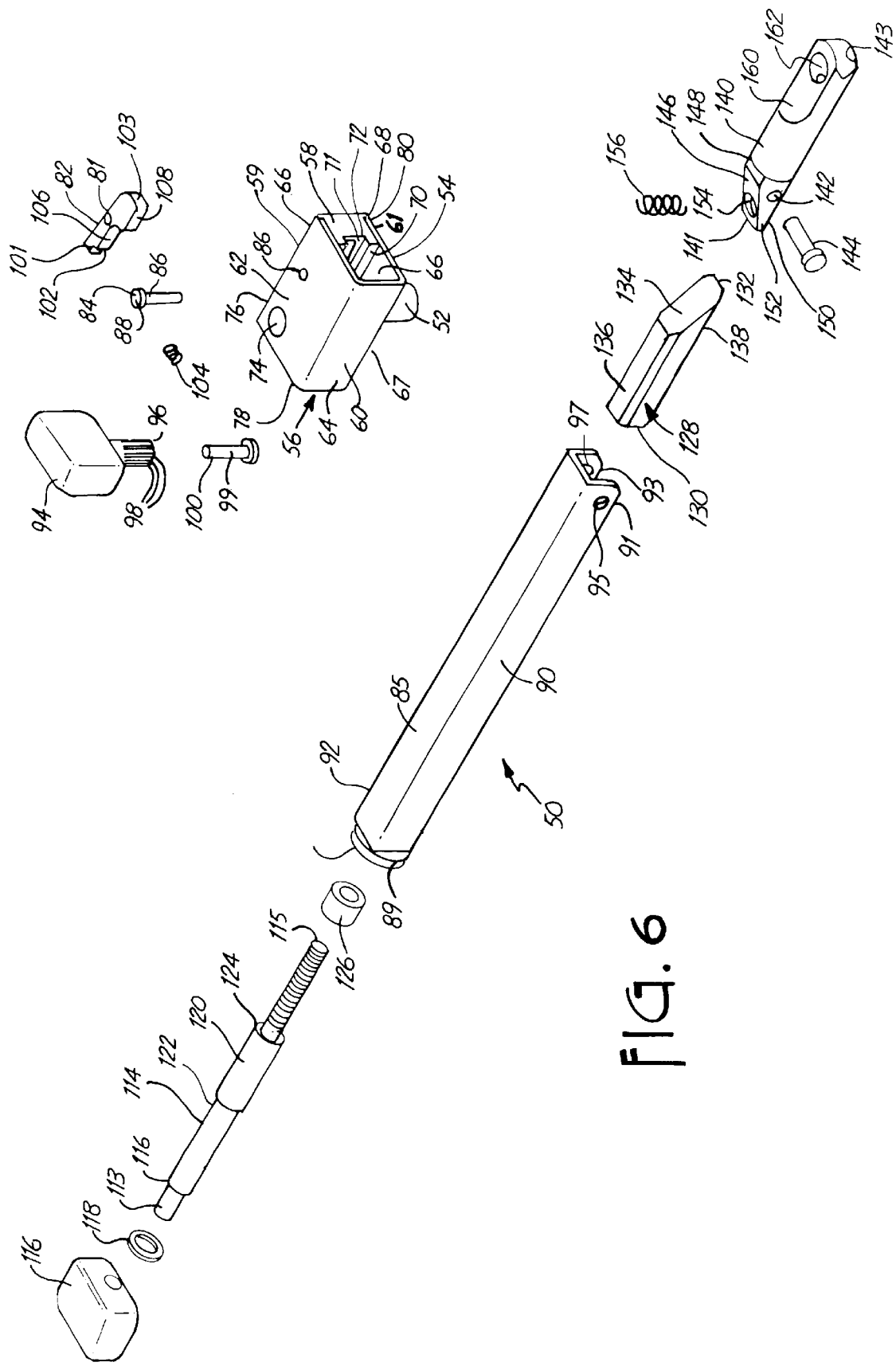
FIG. 6 is an exploded view of the retractor mechanism of the present invention.

Referring to FIGS. 1, 5 and 6, a retractor mechanism 50 is securely positioned on the generally J-shaped member 16 by a cooperation of a pin 52 extending downwardly from a bottom surface 54 of a gearbox assembly 56 with one of the apertures 26 within the generally J-shaped member 16. The pin 52 is in a perpendicular relationship with the bottom surface 54 and extends through a thickness of the generally J-shaped member 16. Preferably, the thickness of the generally J-shaped member 16 is ¼" and the pin 52 is ¾" in length. An end of the pin 52 extends approximately ½ inch below the bottom surface of the generally J-shaped member 16. The excess length of the pin 52 prevents the retractor mechanism 50 from rotating off of the generally J-shaped member 16 when a force is applied to a retractor blade 44, 46 or 200. The only method of removing the retractor mechanism 50 from the generally J-shaped member 16 is to lift the gearbox assembly 56 away from atop surface of the generally J-shaped member 16 until the pin 52 disengages the aperture 26 within the generally J-shaped member 16. While the pin 52 is disposed within the aperture 26, the retractor mechanism 50 is pivotally attached to the generally J-shaped member 16.

The gearbox assembly 56 includes a gearbox casing 58 attached to an outer casing 60. The outer casing 60 is preferably U-shaped and includes the bottom surface 54 to which the pin 52 is attached, a top surface 62 and a first side surface 64. The gearbox casing 58 includes first and second shoulders 66,68 which contact a first end 59 and a second end 61 of the outer casing 60. The shoulders 66, 68 are designed such that each shoulder is even with the top and bottom surfaces 62, 54, when the gearbox casing 58 engages the outer casing 60.

The gearbox casing 58 extends within the outer casing 60 such that a first surface 70 of the gearbox casing 58 and the top surface 62, the bottom surface 54 and the first side wall 64 define a retractor handle bore 66. The retractor handle bore 66 is preferably substantially rectangular in configuration, although other cross-sectional configurations are within the scope of the invention. The retractor handle bore 66 is positioned proximate a second side 67 of the gearbox assembly 56.

A channel 71 is disposed along a length of the first surface 70 of the gearbox casing 58. A pawl retaining cavity 72 is machined into the channel 71 proximate a second end 80 of the gearbox assembly 56. The pawl retaining cavity 72 extends to an outer surface of the gearbox casing 58.

A gear bore 74 is positioned proximate a first side 76 and a first end 78 of the gearbox assembly 56. The gear bore 74 is in a substantially orthogonal relationship with the retractor handle bore 66. The gear bore 74 is in communication with the retractor handle bore 66.

A pawl 82 is inserted into the pawl retaining cavity 72 and retained within the cavity 72 by a cooperation of a pin 84 being inserted into an aperture 86 within the top surface 62, a bore (not shown) which extends into the pawl retaining cavity 72 and a bore 81 through the pawl 82 which is aligned with the bore (not shown) in the gearbox casing 58. Additionally, a bore (not shown) may continue through the pawl retaining cavity 72 to secure an end of the pin 84 within a non-moving part. The pin 84 has an engaging portion 86 proximate a head 88 which creates a frictional engagement of the pin 84 with the bore (not shown) within the gearbox casing 58, thereby retaining the pin 84 within the gearbox assembly 56 and the pawl 82 within the pawl retaining cavity 72.

A retractor handle 90 is disposed through the retractor handle bore 66. The retractor handle 90 is preferably a three sided channel 93 which cooperates with the rectangular retractor handle bore 66. Extending from a first side 92 of the retractor handle is a rack (not shown) of a rack and pinion system (not shown). When the retractor handle 90 is disposed within the retractor handle bore 66, the rack (not shown) extends within the channel 71 of the retractor handle bore 66.

A gear pin 94 is inserted into the gear bore 74 from the top surface of the outer casing 60. A gear 96, having pinions 98 disposed annularly around a circumference of the gear pin 94, is disposed within the gear bore 74 such that the pinions 98 extend into the channel 71 and engage grooves which define the rack (not shown). The gear pin 94 has a bore (not shown) extending from an end which is aligned about a central axis of the gear pin 94. A retaining pin 100 is inserted through an aperture (not shown) within the bottom surface of the outer casing 60 aligned with the bore (not shown) within the gear pin 94 when the gear pin 94 is within the gear bore 74. The retaining pin 100 includes an engaging portion 99 with a slightly larger diameter than the pin which secures the pin 100 within the bore (not shown) of the gear pin 94 thereby securing the gear pin 94 within the gear bore 74.

Figure 3:
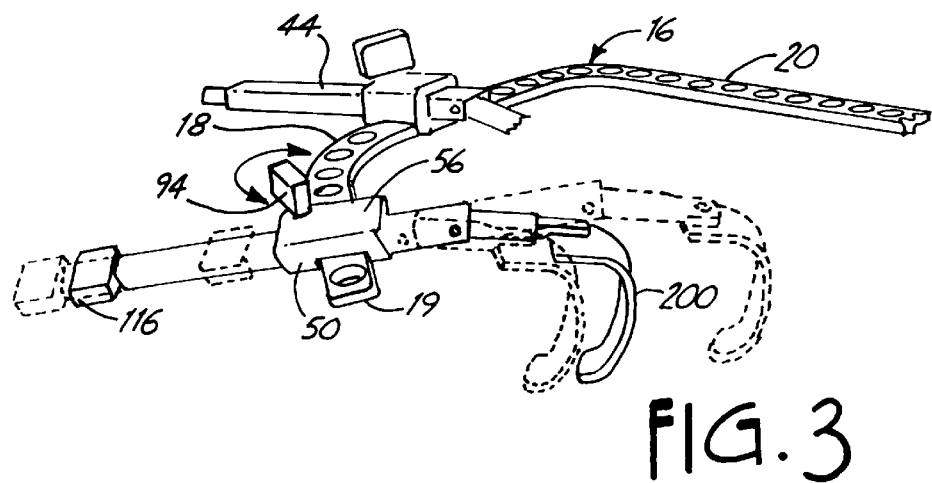
FIG. 3 is a perspective view of a retractor mechanism having a mechanical system for adjusting a longitudinal position of a retractor blade.

A length of the rack (not shown) determines the maximum distance that the retractor handle 90 can be moved through the retractor bore 66 by the manipulation of the rack and pinion system (not shown). The surgeon is easily able to manipulate the position of a retractor blade 21 by rotating the gear pin 94 which in turn rotates the pinions 98 of the gear 96. The interaction of the rotating pinions 98 with the rack (not shown) causes the retractor handle 90 to move longitudinally with respect to the retractor handle bore 66 thereby allowing the surgeon to move the retractor blade 21 laterally into a desired position as best illustrated in FIG. 3.

Referring back to FIG. 6, the pawl 82, which is pivotally attached to the gearbox casing 58 by the pin 84, includes a notch 102 proximate a first end 101. The notch 102 includes a substantially right corner which engages the pinions 98 of the gear 96 such that the gear 96 cannot be rotated in a reverse direction without first displacing the notch 102 from the pinions 98 of the gear 96. The pawl 82 is biased to engage the notch 102 with the pinions by a compression spring 104 engaging a shoulder 106. The spring 104 biases a second end 103 toward an outer edge of the gearbox casing 58 such that the second end 103 extends past the edge of the gear box casing 58. While the second end 103 of the pawl 82 is biased toward the edge, the first end 101 is biased toward the pinions 98. The pawl 102 prevents accidental movement of the retractor handle 90 when the rack and pinion system (not shown) applies a force to the humerus 45 and laterally retracts the humeral ball 43 from the glenoid cavity 41. A length of a surface 108 proximate the second end 103 of the pawl 82 prevents the second end 103 from engaging the grooves defining the rack (not shown).

Referring to FIG. 2, an articulated joint 110 allows the retractor blade 200 to be raised or lowered relative to a blade end 91 of the retractor handle 90 by a pivot pin 112. Referring back to FIG. 6, the retractor handle 90 has a rectangular channel 93 disposed through a length of the retractor handle extending from the blade end 91 to a handle end 89.

A push rod 114 extends through the length of the channel 93 within the retractor handle 91. A first end 113 of the push rod 114 is disposed through an aperture at the handle end 89 of the retractor handle 90. A first shoulder 116 proximate the first end 113 contacts the aperture, thereby fixing the push rod 114 in a selected position with respect to the retractor handle 90 while maintaining rotatability of the push rod 114. A washer 118 is disposed over the first end 113 of the push rod 114 and a knob 116 is fixedly attached to the first end 113 of the push rod 114. The washer 118 prevents the handle end 89 of the retractor handle 90 from goring a surface of the knob 116 and binding the knob 116 to the handle end 89 of the retractor handle 90.

Intermediate the first end 113 and a second end 115 of the push rod 114 is a center portion 120 defining a second shoulder 122 and a third shoulder 124. The center portion 120 has a larger diameter than the diameter of portions adjacent to the center portion 120. The differences in the diameters define the second and third shoulders 122, 124. A spacer 126 is disposed over the second end 115 of the push rod 114. The second end 115 of the push rod 114 is threaded and threadably engages a threaded bore (not shown) within a first end 130 of a first wedge 128.

The first wedge 128 has a substantially rectangular crosssection proximate the first end 130. The rectangular crosssectional portion of the first wedge 128 cooperates with the rectangular channel 93 within the retractor handle 90 which prevents the first wedge 128 from rotating within the rectangular channel 93. Because the first wedge 128 does not rotate when the push rod 114 is rotated, the threadable engagement of the push rod 114 with the bore (not shown) within the first wedge 128 causes the first wedge 128 to move relative to the second end 115 of the push rod 114 when the push rod 114 is rotated. A first wedge surface 134 is defined by a flat surface extending from a top surface 136 to an edge at the bottom surface 138 at a second end 132.

A mounting member 140 includes a bore 142 which aligns with first and second apertures 95, 97 within the first side and a second sides of the retractor handle 90. A pivot pin 144 is inserted through the first aperture 95, the through bore 142 and the second aperture 97 thereby pivotally attaching the mounting member 140 to the retractor handle 90.

Proximate a first end 141 of the mounting member 140 is a second wedge surface 146. The second wedge surface 146 extends from a top surface 148 intermediate the first end 141 and a second end 143 to a bottom surface 150 proximate the first end 141. An angled surface 152 extends upwardly at a slant from the bottom surface 150 toward the first end 141 such that the first end 141 of the mounting member 140 is defined by an edge above the bottom surface 150.

As the push rod 114 is rotated, the second end 132 of the first wedge surface 134 engages the angled surface 152 of the mounting member 140. Further movement of the first wedge surface 134 toward the mounting member 140 causes the mounting member 140 to pivot about the pivot pin 144 while the angled surface 152 travels up the first wedge surface 134. The second wedge surface 146 has a circular recess 154 which cooperates with a compression spring 156. An end of the compression spring 156 rests on a substantially flat, bottom surface of the circular recess 154. Another end of the compression spring 156 is positioned against an inner surface of a top portion 85 of the retractor handle 90.

As the angled surface 152 travels up the first wedge surface 134, the compression spring 156 compresses which biases the angled surface 152 to travel down the first wedge surface 134 as the first wedge 128 is manipulated away from the mounting member 140. One skilled in the art will realize that the second wedge surface 146 allows for greater pivotal movement of the mounting member 140 because the first end 141 of the mounting member 140 will not contact the top portion 85 of the retractor handle 90 until the second wedge surface 146 contacts the top portion 85. One skilled in the art will also recognize that because the mounting member 140 is pivotally attached to the retractor handle 90 between the first end 141 and a second end 143 that as the first end 141 is raised the second end 143 is lowered and vice versa.

Referring to FIG. 7, a cylindrical portion 160 extends from the mounting member 140. A through bore 161 is disposed through the cylindrical portion 160 proximate the second end 143 of the mounting member 140. A shoulder 164 is defined proximate an end of the cylindrical portion 160.

A plug 166 having a bore 168 extending from a first end 170 to a second end 171 is disposed over the cylindrical portion 160 of the mounting member 140 until the first end 170 is adjacent to the shoulder 164. With the first end 170 of the plug adjacent to the shoulder 164, a first slot 172 within a first side surface 176 of a rectangular body 175 and a second slot 174 within a second side surface 178 of the rectangular body 175 are aligned with the through bore 161 within the cylindrical portion 160.

A pin 180 is inserted through the first slot 172, the through bore 161 and the second slot 174. An end of the pin 180 is substantially even with an outer surface of the first side surface 176 and another end of the pin 180 is substantially even with an outer surface of the second side surface 178. Neither end of the pin 180 extends past the outer surfaces of the first and second side surfaces 176, 178. The slots 172, 174 are wider than the diameter of the pin 180 allowing the plug 166 to partially rotate about the cylindrical portion 160 until the pin 180 contacts either surface of the slots 172, 174. Preferably, the plug 166 rotates 10 to 20 degrees about the cylindrical portion 160.

A retractor engaging member 182 having a rectangular bore (not shown) extending from a first end 183 cooperates with the rectangular body 175 of the plug 166. The cooperation of the rectangular body 175 with the rectangular bore (not shown) prevents rotation of the retractor engaging member 182 about the plug 166. The retractor engaging member 182 is slidably positioned on the plug 166 until the first end 181 of the retractor engaging member 182 contacts a shoulder 177 about the plug 166. The outer surface around a perimeter of the shoulder 177 is even with the rectangular outer surface of the retractor engaging member 182.

Proximate a second end 185 of the retractor engaging member 182 is the through bore 162. Extending from an end 201 of a retractor blade 200 is a cylindrical member 202 which cooperates with the through bore 162. The cooperation of the cylindrical member 202 with the through bore 186 allows the retractor blade 200 to rotate about the cylindrical member 202 while being retained therein.

Referring to FIG. 5, the present invention includes the humerus retractor blade 200 attachable to the retractor mechanism 50 by the cooperation of the cylindrical member 202 attached to the blade 200 with the through bore 162 in the retractor blade engaging member 182. The humerus retractor blade 200 resembles a Fakuda blade having a generally flat portion 204 with an arcuate end portion 206 and an aperture 208 disposed within the generally flat portion 204 and extending into the arcuate end portion 206. The aperture 208 in the humerus retractor blade 200 is used to better grip bone and flesh at the surgical site.

Prior to making an incision, the generally J-shaped member 16 and the T-shaped member 28 are adjusted to desired positions by the surgeon. After an incision 13 has been made, the flesh is retracted to expose the shoulder joint 40 by standard retractor blades 44, 46 which are well known in the art. After exposing the shoulder joint 40, the retracting mechanism 50, to which the humerus retractor blade 200 is attached, is positioned in a desired location by inserting the pin 52 extending from the bottom surface 54 of the gearbox assembly 56 into an aperture 26 within the generally J-shaped member 16.

After positioning the retracting mechanism 50 in the desired aperture 26, the gear pin 94 is manipulated to position the humerus retractor blade 200 medially beyond the humerus 45 proximate the humeral head 43 by rotating the gear pin 94. The rotation of the gear pin 94 causes the pinions 98 of the gear 96 to engage the rack (not shown) attached to the retractor handle 90 which causes the retractor handle 90 and the humerus retractor blade 200 to move toward the humerus 45. Once the humerus retractor blade 200 is positioned on a medial side (body side) of the humerus 45 proximate the humeral ball 43, the height of the retractor blade 200 is adjusted.

The height of the humerus retractor blade 200 is adjusted by manipulating the articulated joint 110 by rotating the knob 116 proximate the handle end 89 of the retractor handle 90 as illustrated in FIG. 2. Rotating the knob 116 causes the first wedge 128 to engage the angled surface 152 of the mounting member 140 causing the first end 141 of the mounting member 140 to rise up the first wedge 128. As the first end 141 rises up the first wedge 128, the second end 143 of the mounting member 140 pivots downward about the pin 144. The second end 143 is pivoted downward until the arcuate end 206 of the humerus retractor blade 200 is positioned about the humerus 45 on a medial side of the humerus 45. The position of the humerus retractor blade 200 can be slightly adjusted by rotating the retractor engaging member 182 about the cylindrical portion 160 of the mounting member 140.

With the arcuate end portion 206 of the humerus retractor blade 200 in the desired location, the gear pin 94 is rotated in an opposite direction thereby causing the mechanical system, preferably but not limited to a rack and pinion system (not shown), to move the retractor handle 90 and the humerus retractor blade 200 laterally, as illustrated in FIG. 3, away from the shoulder joint 40. The humerus retractor blade 200 is used to retract the humerus 45 after separation from the humeral ball 43 or after the humeral ball 43 is dislocated from the glenoid cavity 41 but prior to being separated from the humerus 45. As the retractor blade 200 is moved away from the shoulder joint 40 by the rack and pinion system (not shown), a lateral force is applied to the humerus 45 until the humerus 45 is displaced a desired distance from the glenoid cavity 41. With the humeral ball 43 displaced from the glenoid cavity 41, the humeral ball 43 is replaced and an insert is disposed within the glenoid cavity 41 to repair the glenoid cavity 41.

The pawl 82 engages the pinions 98 of the gear 96, preventing the retractor handle 90 from inadvertently moving toward the shoulder joint 40 and releasing the force applied by the humerus retractor blade 200. Additionally, the pawl 82 allows the surgeon to rest if needed during the surgical procedure without having to reapply the force already exerted upon the humerus 45.

The use of the mechanically adjustable retractor mechanism 50 allows the humerus 45 to be displaced from the glenoid cavity 41 using a minimum amount of force and a minimum amount of movement as necessary to perform the shoulder replacement surgery. Using only the required force and minimizing movement reduces the amount of trauma to the patient and reduces the amount of time required to recover.

Additionally, the use of the humerus retractor blade 200 along with the retractor mechanism 50 to laterally retract the humerus 45 from the glenoid cavity 41 reduces the number of surgeons required to perform the surgical procedure. The reduction in personnel required to perform the surgery is possible because a surgeon is not needed to provide a force to displace the humerus 45 laterally from the glenoid cavity 41. Rather, the rack and pinion system (not shown) is used in the place of additional surgical personnel which provides the surgeon with better access to the limited surgical site.

Once the necessary procedures have been performed on the glenoid cavity 41 and the humerus 45, the pawl 82 is disengaged from the gear pinions 98 and the rotation of the gear pin 94 is reversed to manipulate the rack and pinion system (not shown) which, in turn, positions the humeral ball 43 proximate the glenoid cavity 41. With the humeral ball 43 proximate the glenoid cavity 41, the humerus retractor blade 200 is disengaged from the humerus 45. Once the humerus retractor blade 200 disengages the humerus 45, the surgeon raises the pin 52 from the aperture 26 thereby removing the retractor mechanism 50 from the surgical site. With the implanted humeral ball 43 adjacent to the repaired glenoid cavity 41, the surgeon forces the humeral ball 43 into the surgically repaired glenoid cavity 41.

Although the present invention has been described with reference to preferred embodiments, workers skilled in the art will recognize that changes may be made in form and detail without departing from the spirit and scope of the invention.

What is claimed is:

1. A method of performing surgery on a shoulder joint using at least one support arm attached to a retractor support apparatus, the shoulder joint includes a glenoid cavity, a humerus and a humeral ball attached to the humerus and positioned within the glenoid cavity, the method comprising:
    incising a patient to expose the shoulder joint;
    dislocating the humeral ball from the glenoid cavity;
    mounting a proximal end of a humerus retractor on the one support arm wherein the humerus retractor comprises a humerus retractor blade at a distal end;
    positioning the humerus retractor about the humerus; and
    retracting the humeral ball laterally away from the glenoid cavity with a mechanical mechanism of the humerus retractor thereby providing access to the glenoid cavity and the humeral ball.

2. The method of claim 1 and further comprising separating the humeral ball from the humerus.

3. The method of claim 2 and further comprising sawing the humeral ball from the humerus.

4. The method of claim 2 and further comprising:
    hollowing a cavity into a freshly separated surface of the humerus;
    disposing a stem having a ball attached thereto into the cavity in the humerus; and
    securing the stem within the cavity such that the ball is fixed into position on the humerus.

5. The method of claim 4 and further comprising securing an insert within the glenoid cavity.

6. The method of claim 5 and further comprising disposing the ball attached to the humerus within the insert secured within the glenoid cavity.

7. The method of claim 2 wherein the positioning of the humerus retractor further comprises:
    manipulating the mechanical system, wherein the mechanical system comprises a rack and pinion system, to adjust a longitudinal position of the humerus retractor blade such that the humerus retractor blade, including a substantially flat portion, an arcuate end portion and an aperture therein, extends beyond a medial surface of the humerus;
    manipulating a vertical adjustment system, wherein the vertical adjustment system comprises an articulated joint, to lower the arcuate end portion of the humerus retractor blade below the humerus such that the aperture within the humerus retractor blade is vertically aligned with the humerus; and
    manipulating the rack and pinion system of the mechanical system such that the humerus retractor blade including the aperture engages the humerus.

8. The method of claim 7 wherein the lateral retraction of the humerus from the glenoid cavity further comprises manipulating the rack and pinion system of the mechanical system to displace the humeral head from the glenoid cavity to provide access thereto.

9. The method of claim 8 and further comprising:
    disengaging a pawl from the rack and pinion system; and
    manipulating the rack and pinion system such that the humeral ball attached to the humerus is positioned proximate the glenoid cavity.

10. The method of claim 9 and further comprising:
    manipulating the articulated joint such that the humeral ball is juxtaposed to the glenoid cavity; and
    manipulating the rack and pinion system to disengage the humerus retractor blade from the humerus.

11. The method of claim 10 and further comprising inserting the humeral ball within the glenoid cavity.

12. The method of claim 1 and wherein the positioning of the support arm comprises:
    disposing a generally J-shaped support arm within a retractor support mounted to a surgical table; and
    disposing a T-shaped member having a plurality of pegs extending downward into a plurality of apertures within the generally J-shaped support arm wherein the T-shaped member and generally J-shaped support arm provides access to the surgical site.

13. A method of minimizing a force required to prepare a shoulder joint for a shoulder surgery, the shoulder joint including a glenoid cavity, a humerus, and a humeral ball attached to the humerus wherein the humeral ball is disposed within the glenoid cavity, the method comprising:
    incising a patient;
    retracting the incision to expose the shoulder joint;
    dislocating the humeral ball from the glenoid cavity;
    positioning a support arm on a retractor support;
    operably connecting a humerus retractor to the support arm;
    engaging the humerus with the humerus retractor; and
    applying a force to the humerus with a mechanical system of the humerus retractor until the humeral head is laterally displaced a selected distance from the glenoid cavity thereby providing access to the glenoid cavity and the humeral ball.

14. The method of claim 13 and further comprising separating the humeral ball from the humerus.

15. The method of claim 14 and further comprising sawing the humeral ball from the humerus.

16. The method of claim 13 and further comprising:
hollowing a cavity into a freshly separated surface of the humerus;
disposing a stem having a ball attached thereto into the cavity in the humerus; and
securing the stem within the cavity such that the ball is fixed into position on the humerus.

17. The method of claim 16 and further comprising securing an insert within the glenoid cavity.

18. The method of claim 17 and further comprising disposing the ball attached to the humerus within the insert secured within the glenoid cavity.

19. The method of claim 13 wherein the engaging of the humerus with the humerus retractor further comprises:
manipulating the mechanical system, wherein the mechanical system comprises a rack and pinion system, to adjust a longitudinal position of the humerus retractor blade, the humerus retractor blade comprising a flat portion, an arcuate distal end and an aperture disposed within the humerus retractor blade, such that the humerus retractor blade extends beyond a medial surface of the humerus;
manipulating a vertical adjustment system, wherein the vertical adjustment system comprises an articulated joint, to lower the arcuate distal end of the humerus retractor blade below the humerus such that the aperture within the humerus retractor blade is vertically aligned with the humerus; and
manipulating the rack and pinion system of the mechanical system such that the humerus retractor blade including the aperture engages the humerus.

20. The method of claim 19 wherein the lateral displacement of the humerus from the glenoid cavity further comprises manipulating the rack and pinion system of the mechanical system to displace the humeral head from the glenoid cavity to provide access thereto.

21. The method of claim 20 and further comprising:
disengaging a pawl from the rack and pinion system; and
manipulating the rack and pinion system such that the humeral ball attached to the humerus is positioned proximate the glenoid cavity.

22. The method of claim 21 and further comprising:
manipulating the articulated joint such that the humeral ball is juxtaposed to the glenoid cavity; and
manipulating the rack and pinion system to disengage the humerus retractor blade from the humerus.

23. The method of claim 22 and further comprising inserting the humeral ball within the glenoid cavity.

24. The method of claim 13 and wherein the positioning of the support arm comprises:
disposing a generally J-shaped support arm within a retractor support mounted to a surgical table; and
disposing a T-shaped member having a plurality of pegs extending downward into a plurality of apertures within the generally J-shaped support arm wherein the T-shaped member and the generally J-shaped support arm provide access to the surgical site and support the retractors.

25. A method of reducing a number of surgical personnel required to perform a surgical procedure on a shoulder joint, the shoulder joint including a glenoid cavity, a humeral ball disposed within the glenoid cavity and a humerus extending from the humeral ball, the method comprising:
incising a patient so as to expose the shoulder joint;
dislocating the humeral ball from the glenoid cavity;
positioning a humerus retractor on a support; and
manipulating a mechanical system within the humerus retractor such that a humerus retracting blade of the humerus retractor engages the humerus such that a movement of the humerus retractor blade produces a force which displaces the humeral ball from the glenoid cavity.

26. The method of claim 25 wherein the support includes a generally J-shaped member and a T-shaped member operably attached to the generally J-shaped member and further comprising positioning the generally J-shaped member and the T-shaped member in a selected retracting position.

27. The method of claim 25 and further comprising maintaining the force on the humerus with a pawl cooperating with the mechanical system comprising a rack and pinion system thereby reducing the need for another person to maintain constant force on the humerus during the surgical procedure.

28. The method of claim 25 and further comprising separating the humeral ball from the humerus.

29. The method of claim 28 and farther comprising sawing the humeral ball from the humerus.

30. The method of claim 28 and further comprising:
hollowing a cavity into a freshly separated surface of the humerus;
disposing a stem having a ball attached thereto into the cavity in the humerus; and
securing the stem within the cavity such that the ball is fixed into position on the humerus.

31. The method of claim 30 and further comprising securing an insert within the glenoid cavity.

32. The method of claim 31 and further comprising:
manipulating a rack and pinion system to position the humeral ball proximate the glenoid cavity; and
disengaging the humerus retractor from the humerus.

33. The method of claim 32 and further comprising disposing the ball attached to the humerus within the insert secured within the glenoid cavity.

34. A method of performing a surgical procedure on a shoulder joint, the shoulder joint includes a glenoid cavity, a humerus and a humeral ball attached to the humerus and positioned within the glenoid cavity, the method comprising:
positioning a patient on a surgical table;
mounting a support apparatus to the surgical table;
attaching a first retractor support arm to the support apparatus;
positioning the first retractor support arm about the shoulder joint;
attaching a second retractor support arm to the first retractor support arm such that the first and second retractor support arms provide access to the shoulder joint;
incising the flesh of the patient about the shoulder joint;
attaching a first retractor having a first retractor blade to the first retractor support arm;
attaching a second retractor having a second retractor blade to the second retractor support arm;
positioning the first and second retractor blade within the incision; and
retracting the flesh of the patient from the shoulder joint with the first and second retractor blades such that the shoulder joint is exposed.

35. The method of claim 34 and further comprising:
disposing a humerus retractor on the first support arm; and positioning the humerus retractor about the humerus with a mechanical system within the humerus retractor.

36. The method of claim 35 and further comprising separating the humeral ball from the humerus.

37. The method of claim 36 and further comprising sawing the humeral ball from the humerus.

38. The method of claim 36 and further comprising:
hollowing a cavity into a freshly separated surface of the humerus;
disposing a stem having a ball attached thereto into the cavity in the humerus; and
securing the stem within the cavity such that the ball is fixed into position on the humerus.

39. The method of claim 38 and further comprising securing an insert within the glenoid cavity.

40. The method of claim 39 and farther comprising disposing the ball attached to the humerus within the insert secured within the glenoid cavity.

41. The method of claim 35 wherein the positioning of the humerus retractor further comprises:
manipulating the mechanical system, wherein the mechanical system comprises a rack and pinion system, to adjust a longitudinal position of the humerus retractor blade such that the humerus retractor blade including a substantially flat portion, an arcuate end portion and an aperture therein, extends beyond a medial surface of the humerus;
manipulating a vertical adjustment system, wherein the vertical adjustment system comprises an articulated joint, to lower the arcuate end portion of the humerus retractor blade below the humerus such that the aperture within the humerus retractor blade is vertically aligned with the humerus; and
manipulating the rack and pinion system of the mechanical system such that the humerus retractor blade including the aperture engages the humerus.

42. The method of claim 41 and further comprising retracting the humerus laterally from the glenoid cavity, wherein the lateral retraction comprises manipulating the rack and pinion system of the mechanical system to displace the humeral head from the glenoid cavity to provide access thereto.

43. The method of claim 42 and further comprising:
disengaging a pawl from the rack and pinion system; and
manipulating the rack and pinion system such that the humeral ball attached to the humerus is positioned proximate the glenoid cavity.

44. The method of claim 43 and further comprising:
manipulating the articulated joint such that the humeral ball is juxtaposed to the glenoid cavity; and
manipulating the rack and pinion system to disengage the humerus retractor blade from the humerus.

45. The method of claim 44 and further comprising inserting the humeral ball within the glenoid cavity.

46. The method of claim 34 and wherein the positioning of the first support arm comprises:
disposing the first support arm, the first support arm being generally J-shaped, within the retractor support mounted to a surgical table; and
rotating the retractor support mounted to the surgical table to position the first support arm about the shoulder joint.

47. The method of claim 46 and wherein the attaching of the second support arm to the first support arm further comprises disposing a plurality of pegs within the second support arm into a plurality of apertures within the generally J-shaped first support arm and wherein the second support arm is generally T-shaped such that the generally J-shaped first support arm and the generally T-shaped second support arm provide access to the surgical site.

48. The method of claim 34 wherein the retraction of the flesh by the first and second retractors comprises:
manipulating a mechanical system within each of the first and second retractors, wherein each mechanical system comprises a rack and pinion system, to adjust a longitudinal position of first and second retractor blades such that the first and second retractor blades are positioned above the incision;
manipulating a vertical adjustment system within each of the first and second retractors, wherein each vertical adjustment system comprises an articulated joint, to lower the first and second retractor blades into the incision; and
manipulating each rack and pinion system of the mechanical system of the first and second retractors such that the severed flesh is retracted from the incision to expose the shoulder joint.

* * * * *

UNITED STATES PATENT AND TRADEMARK OFFICE
CERTIFICATE OF CORRECTION

PATENT NO. : 6,368,271 B1
DATED : April 9, 2002
INVENTOR(S) : Todd W. Sharratt

It is certified that error appears in the above-identified patent and that said Letters Patent is hereby corrected as shown below:

Column 2,
Line 17, delete "reduced", insert -- reducted --

Column 4,
Line 23, delete "atop", insert -- a top --
Line 34, delete "66,68", insert -- 66, 68 --
Line 42, delete "defme", insert -- delete --

Column 12,
Line 21, delete "farther", insert -- further --

Column 13,
Line 16, delete "farther", insert -- further --

Signed and Sealed this

Twenty-fifth Day of June, 2002

Attest:

JAMES E. ROGAN
Attesting Officer  Director of the United States Patent and Trademark Office